US012168030B2

(12) United States Patent
McIntosh et al.

(10) Patent No.: US 12,168,030 B2
(45) Date of Patent: Dec. 17, 2024

(54) **METHOD FOR PRODUCING STABLE *Actinidia deliciosa* POWDER WITH HIGH LEVEL BIOACTIVE ACTINIDIN ENZYME**

(71) Applicant: Waitaki Biosciences, Christchurch (NZ)

(72) Inventors: Craig Lachlan McIntosh, Christchurch (NZ); Raumiria Pohatu, Christchurch (NZ)

(73) Assignee: WAITAKI BIOSCIENCES, Christchurch (NZ)

(*) Notice: Subject to any disclaimer, the term of this patent is extended or adjusted under 35 U.S.C. 154(b) by 179 days.

(21) Appl. No.: 17/166,515

(22) Filed: Feb. 3, 2021

(65) Prior Publication Data

US 2021/0322500 A1 Oct. 21, 2021

Related U.S. Application Data

(60) Provisional application No. 62/969,952, filed on Feb. 4, 2020.

(51) Int. Cl.

| | |
|---|---|
| ***A23L 19/00*** | (2016.01) |
| ***A61K 36/185*** | (2006.01) |
| ***A61K 38/48*** | (2006.01) |

(52) U.S. Cl.

CPC ........ *A61K 36/185* (2013.01); *A61K 38/4873* (2013.01); *A61K 2236/15* (2013.01); *A61K 2236/17* (2013.01); *A61K 2236/51* (2013.01)

(58) Field of Classification Search

CPC .............. A61K 36/185; A61K 38/4873; A61K 2236/15; A61K 2236/17; A61K 2236/51

See application file for complete search history.

(56) References Cited

U.S. PATENT DOCUMENTS 6,971,187 B1 * 12/2005 Pikal ........................ F26B 5/06 34/92

2010/0143319 A1 6/2010 Weir

FOREIGN PATENT DOCUMENTS

| | | | |
|---|---|---|---|
| WO | 2008023266 | A2 | 2/2008 |
| WO | 2008136689 | A1 | 11/2008 |
| WO | 2012158048 | A1 | 11/2012 |

OTHER PUBLICATIONS

Hammami, Chokri, and Frédéric René. "Determination of freeze-drying process variables for strawberries." Journal of food Engineering 32.2 (1997): 133-154 (Year: 1997).*

(Continued)

*Primary Examiner* — Louise W Humphrey
*Assistant Examiner* — Mary A Crum
(74) *Attorney, Agent, or Firm* — Venable LLP; Keith G. Haddaway

(57) ABSTRACT

A method for producing stable and bioavailable *Actinidia deliciosa* powder from kiwifruit, including drying kiwifruit pulp to form dried pulp, separately drying kiwifruit skin to form a dried skin, measuring the insoluble fiber content of the dried pulp and the dried skin, and making a blend by adding the dried skin to the dried pulp in an amount to obtain an insoluble fiber content of 10-15% in the blend. The *Actinidia deliciosa* powder is free of artificial additives, anti-caking agents, or flow agents and has a moisture content of less than about 2.5%.

11 Claims, 3 Drawing Sheets

CIRC. SET POINT (°C)
PRODUCT (°C)
PRESSURE (bar)
CONDENSER (bar)
TEMPERATURE (°C)
PRESSURE (BAR)
TIME (HOURS)

(56) References Cited

OTHER PUBLICATIONS

Calskan, Gulsah, Kadriye Ergun, and S. Nur Dirim. "Freeze drying of kiwi (*Actinidia deliciosa*) puree and the powder properties." Italian Journal of Food Science 27.3 (2015): 385-396 (Year: 2015).*
Vikumer, "what's conductive heating and radiative heating in freeze drying?" (Year: 2023).*
Froilabo, "Blog Blast Freezer" (Year: 2023).*
Zhuang, Ziqi, et al. "The manufacturing process of kiwifruit fruit powder with high dietary fiber and its laxative effect." Molecules 24.21 (2019): 3813 (Year: 2019).*
Silva-Espinoza, Marilú A., et al. "The impact of freeze-drying conditions on the physico-chemical properties and bioactive compounds of a freeze-dried orange puree." Foods 9.1 (2019): 32 (Year: 2019).*
Richards, Eric. "Characterisation of bioactive proteins present in *Actinidia* species", University of Canterbury, 2014 (Year: 2014).*
Nowak, Dorota, et al. "The freeze-drying of foods—The characteristic of the process course and the effect of its parameters on the physical properties of food materials." Foods 9.10 (2020): 1488 (Year: 2020).*
Ansell et al. (May 1, 2015), "Kiwifruit-derived supplements increase stool frequency in healthy adults: a randomized, double-blind, placebo-controlled study", Nutrition Research, vol. 35, No. 5, pp. 401-408.
Soqueeta et al. (Dec. 10, 2015), "Characterization of physiochemical and microbiological properties, and bioactive compounds, of flour made from the skin and bagasse of kiwi fruit (*Actinidia deliciosa*)", Food Chemistry, vol. 199, pp. 471-478.
Han KS, et al. (2011), "Green kiwifruit modulates the colonic microbiota in growing pigs", Letters in Applied Microbiology, vol. 52, pp. 379-385.
Vesterlund S. et al. (2012), "Water activity in dry foods containing live probiotic bacteria should be carefully considered: A case study with Lactobacillus rhammnosus GG in Flexseed", International Journal of Food Microbiology, vol. 157, pp. 319-321.
Neha A. et al. (2012), "Probiotic: as effective treatment of diseases." International Research Journal of Pharmacy, vol. 3, pp. 96-101.
Schroder R. et al. (2001), "Purification and characterization of a galactoglucomanna from kiwifruit (*Actinidia deliciosa*)", Carbohydrate Research, vol. 331, pp. 291-306.
Cal-Vidal J. et al. (1985), "Processing conditions affecting the hygroscopic behavior of freeze-dried passion fruit juice", Journal of Food Science, vol. 50, pp. 1238-1241.
Commisso et al. (2019), "Untargeted and targeted metabolomics and tryptophan decarboxylase in vivo characterization provide novel insight on the development of kiwifruits (*Actinidia deliciosa*)", Int. J. Mol. Sci, vol. 20, 897 (23 pages).
Udani et al. (2013), "Effects of kivia powder on gut health in patients with occasional constipation: a randomized, double-blind, placebo-controlled study", Nutrition Journal, vol. 12, 78 (10 pages).
Kindleysides et al. (2015), "Encapsulated green kiwifruit extract: a randomised controlled trial investigating alleviation of constipation in otherwise healthy adults", Asia Pac. J. Clin. Nutr., vol. 24, pp. 421-429.
International Search Report and Written Opinion issued in corresponding International Application No. PCT/IB2021/050926 on Jun. 10, 2021.

* cited by examiner

METHOD FOR PRODUCING STABLE *Actinidia deliciosa* POWDER WITH HIGH LEVEL BIOACTIVE ACTINIDIN ENZYME

PRIORITY

This application claims priority to U.S. provisional application 62/969,952 filed Feb. 4, 2020, the entire contents of which are incorporated by reference.

BACKGROUND OF THE INVENTION

Field of the Invention

The present invention relates to nutritional and dietary supplements. More specifically, the present invention is a method for producing stable *Actinidia deliciosa* powder from kiwifruit. More particularly, the invention is a method for producing *Actinidia deliciosa* powder with a high bioactivity of actinidin enzyme.

Description of the Background of the Invention

Green kiwifruit (*Actinidia deliciosa*) is one of the most nutrient dense fruits in the world and contains a high level of prebiotic fiber. Prebiotic fiber is a non-digestible part of foods that provide health benefits when consumed. Prebiotic fiber goes through the small intestine undigested and is fermented when it reaches the large colon. This fermentation process feeds beneficial bacteria colonies and helps to increase the number of desirable bacteria in the digestive system and improve or restore the gut flora. As a result, consuming prebiotic fiber products can reduce gastrointestinal discomfort, improve immune health, relieve constipation, and provide other health benefits.

Green kiwifruit is known to provide a large range of other health benefits, such as improving the immune system and relieving chronic constipation, attributed to the high levels of dietary fiber, antioxidants and Vitamin C. Studies have also shown that consuming green kiwifruit has gastrointestinal benefits by modulating colonic microbiota. The key to the kiwifruit's benefit lies in actinidin, a naturally potent proteolytic enzyme that enhances protein digestion. In vitro studies have shown that actinidin enhances the digestion of a number of different food proteins, such as soy, red meat, milk, gluten, and gliadin. Therefore, consumption of actinidin may also improve one's gut motility, which is an important contributor to improving bowel function.

Furthermore, kiwi fruit is a source of lutein, a carotenoid present in high concentrations in the retina, and plays an important role in maintaining the health of the eyes. Specifically, lutein's antioxidant activity protects the retina from oxidative damage by scavenging reactive oxygen species and filtering blue light.

Kiwifruit is also a source of serotonin, and one possible mechanism by which kiwi fruit extracts its benefit on the gastrointestinal tract (GIT) may be via increased serotonin production. Although most strongly associated with being a neurotransmitter in the central nervous system, the primary site of serotonin synthesis, storage and release is the GIT. From the mucosa, serotonin is released within the GIT, where it may activate neural reflexes associated GIT function (secretions, motility and vasodilation). By increasing serotonin levels, beneficial effects on the GIT may be possible. However, the effects kiwi fruit have on serotonin levels to date were previously unknown.

Dried kiwifruit powder and kiwifruit extracts are commercially available. The effect of kiwi fruit extract on functional gastrointestinal disorders in humans has been previously studied. Udani and Bloom (Nutrition Journal 2013, 12:78) evaluated the efficacy of a kiwi fruit extract versus placebo on constipation and overall gut health in 87 adults over 4 weeks. The product studied was identified as Kivia powder containing "Zyactinase™." A dose of 5.5 g kiwi fruit extract was taken daily. Results of the study showed a significant improvement in spontaneous and complete bowel movements in the treatment group along with reducing abdominal pain and flatulence compared to placebo. Kindleysides et al (Asia Pac J Clin Nutr 2015; 24(3):421-429) evaluated 1 g/day of encapsulated kiwifruit extract compared to placebo in 40 adults experiencing constipation over 3 weeks. The product tested was an extract of flesh, skin and seeds of the whole kiwifruit. Results of the study showed no improvement in bowel motion frequency or other parameters. The authors concluded a higher dose may be required to see a beneficial result. Furthermore, Ansell et al. (Nutrition Research 2015 35:401-408) studied the effect of Actazin and Gold, 2 powdered ingredients derived from whole New Zealand green and gold kiwifruit on stool frequency in 19 adults. The Actazin and Gold powders tested contained 40700 AUs/g and 9100 AUs/g actinidin, respectively. Along with placebo and Gold (2400 mg/day) there were two dosing regimes for the Actazin, specifically 600 mg (Actazin low dose) and 2400 mg/day (Actazin high dose), each administered as a single dose over 28 days. Results of the study showed both Actazin (2400 mg/day) and Gold (2400 mg/day) significantly increases daily bowel motions by more than 1 bowel movement per week and was well tolerated.

The benefits of dried kiwifruit powder are diminished if the product lacks actinidin activity and activity can further diminish over time upon storage. Typically, a manufacturer derives the dried kiwifruit powder using freeze drying or spray drying to isolate actinidin. Dried kiwifruit powder is hydroscopic and can easily absorb water and result in the growth of microbial bacteria. In particular, a water activity reading of 0.6 or higher in the dried powder can dramatically increase the chance of microbial growth. Therefore, it is important to maintain a low level of water activity in the dried powder. To do so, manufacturers typically add excipients, such as silica (silicon dioxide) or cellulose, to the dried kiwifruit powder to limit water activity by absorbing water to prevent clumping of the powdered product to ensure fine flowing powders. While generally considered safe to consume, scientists have warned that these additives could be harmful to the body. Customers desire a product that is free of additives or excipients.

Another challenge of the traditional freeze drying or spray drying of *Actinidia deliciosa* is that the level of actinidin enzyme in the final product is either lower than desired or varies from batch to batch. This inconsistency of the actinidin enzyme activity creates a challenge to develop a method for producing a predictable product.

Therefore, there is a need for an all-natural *Actinidia deliciosa* powder. A method for producing stable *Actinidia deliciosa* powder from green kiwifruit that contains high levels of bioactive actinidin enzyme is also needed. There is a further need for a method for producing *Actinidia deliciosa* powder that does not contain any excipients and achieves high bioactive actinidin enzyme activity. Furthermore, there is a need to develop a method that provides reproducible activity of *Actinidia deliciosa* powder products.

BRIEF SUMMARY OF THE INVENTION

Antibiotics and poor diets have impacted the gastrointestinal health of individuals. In particular, antibiotics have destroyed the natural gut flora in a body. As a result, people experience various dietary issues, including inability to digest certain food proteins, resulting in diarrhea and/or malnutrition. Prebiotic fiber is believed to be able to restore the gut flora by modulating the gastrointestinal microbes in the body. Green kiwifruit contains the enzyme actinidin that can aid with protein digestion. As such, the present invention is directed to a method for producing stable and bioavailable *Actinidia deliciosa* powder from kiwifruit. The *Actinidia deliciosa* powder can be used as a health supplement in powdered form or as pills or tablets.

One aspect of the present invention provides an all-natural dried *Actinidia deliciosa* powder from kiwifruit. The dried *Actinidia deliciosa* powder is low in moisture and does not contain any additives or preservatives, but maintains the free-flowing character by using a blend of dried kiwifruit skin and dried kiwifruit pulp. Surprisingly and unexpectedly, the use of the dried kiwifruit skin provides the final blended product with the needed flowability, while preventing the need for using any excipients or anti-caking agents. In addition, the kiwifruit skin contains insoluble fiber and other beneficial micronutrients, such as polyphenols and antioxidants. Thereby, the invention provides an all-natural supplement that is needed in the marketplace.

The desired blend of the *Actinidia deliciosa* powder is achieved by using a combination dried kiwifruit pulp and dried kiwifruit skin. The kiwifruit pulp and the kiwifruit skin are dried separately, for example, by freeze drying using radiant and conductive heating methods, respectively, in multi-stage drying sequences. The multi-stage drying sequences of the method allow the *Actinidia deliciosa* powder to retain a higher actinidin enzyme activity in the blended product. The invention provides advantages that were not previously appreciated and satisfies a long felt need for an all-natural *Actinidia deliciosa* powder with high level of actinidin enzyme activity.

Another aspect of the invention includes blending dried kiwifruit skin with dried kiwifruit pulp to obtain an insoluble fiber content of 10-15%. The invention includes drying kiwifruit pulp to form a dried pulp, separately drying kiwifruit skin to form a dried skin, measuring the insoluble fiber content of the dried pulp and the dried skin, and making the blend by adding the dried skin to the dried pulp in an amount to obtain an insoluble fiber content of 10-15% in the blend. The invention also includes milling the blend and forming into a tablet or filling the blend into a capsule.

In another aspect of the present invention, the pulp is dried, for example freeze dried, using radiant heat in various stages and each stage varies in temperature and time. For example, in one embodiment of the present invention, a first stage at 30° C. for 60 minutes; a second stage at 50° C. for 250 minutes; a third stage at 60° C. for 580 minutes; a fourth stage at 50° C. for 1320 minutes; a fifth stage at 40° C. for 640 minutes; and a sixth stage at 30° C. for 30 minutes. The size of the batch can vary depending on the capacity of the drier. In embodiments, the pulp is freeze-dried under vacuum at a pressure between 45 Pa (0.00045 Bar) to 20 Pa (0.0002 Bar). In another embodiment of the present invention, the pulp is dried to a water activity of less than about 0.3 or a moisture level of less than about 2.5%. The dried pulp has an enzyme activity of at least 150,000 AU/g. The invention includes forming a minced kiwifruit pulp by mincing the pulp at a temperature of less than about −18° C. before drying the pulp. The invention further includes blast freezing the minced kiwifruit pulp before freeze drying to a temperature of less than about −30° C. in a period of less than about 3 hours. The invention also includes maintaining the minced kiwifruit pulp at a temperature of less than about −30° C. for at least 4 hours before freeze drying the pulp. According to the present invention, the minced kiwifruit pulp is maintained at a temperature of less than about −30° C. for about 10 to about 14 hours.

In another aspect of the present invention, the kiwifruit skin is minced, for example to a size of about 16 mm, followed by drying using, for example, freeze drying. In embodiments, the skin is freeze dried using conductive heat in various stages and each stage varies in temperature and time. In an exemplary embodiment, freeze drying the skin includes, a first stage at 10° C. for 180 minutes, a second stage at 70° C. for 1020 minutes, a third stage at 60° C. for 420 minutes, and a fourth stage at 50° C. for 90 minutes. The skin is freeze dried under vacuum at a pressure of less than 0.002 bar. The skin is dried to a water activity of less than about 0.2 or a moisture level of less than about 1%.

In another aspect, the present invention relates to a stable and bioavailable *Actinidia deliciosa* powder including dried kiwifruit pulp and dried kiwifruit skin. In an exemplary embodiment of the invention, the powder has an insoluble fiber content of 10-15%. In exemplary embodiments, the powder does not contain any excipients, such as silica dioxide, cellulose, magnesium stearate, or isomalt.

In an exemplary embodiment of the invention, the powder has an actinidin enzyme activity (i.e. activity units, AU) of from about 50,000 AU/g to about 200,000 AU/g, from about 50,000 AU/g to about 165,000 AU/g, or from about 100,000 AU/g to about 150,000 AU/g. In exemplary embodiments, the actinidin enzyme activity is at least about 100,000 AU/g, preferably at least about 120,000 AU/g.

In another aspect, the present invention relates to a composition comprising a stable and bioavailable *Actinidia deliciosa* powder including dried kiwifruit pulp and dried kiwifruit skin. In an exemplary embodiment of the invention, the composition is in the form of a tablet or capsule. In exemplary embodiments, the composition is free of artificial additives, anti-caking agents, or flow agents. In exemplary embodiments, the composition is substantially free of cellulose, silica, magnesium stearate, isomalt and other excipients.

Further objectives and advantages, as well as the structure and function of preferred embodiments will become apparent from a consideration of the description, drawings, and examples.

BRIEF DESCRIPTION OF THE DRAWINGS

The foregoing and other features and advantages of the invention will be apparent from the following, more particular description of a preferred embodiment of the invention, as illustrated in the accompanying drawings wherein like reference numbers generally indicate identical, functionally similar, and/or structurally similar elements.

DETAILED DESCRIPTION OF THE INVENTION

Figure 1:
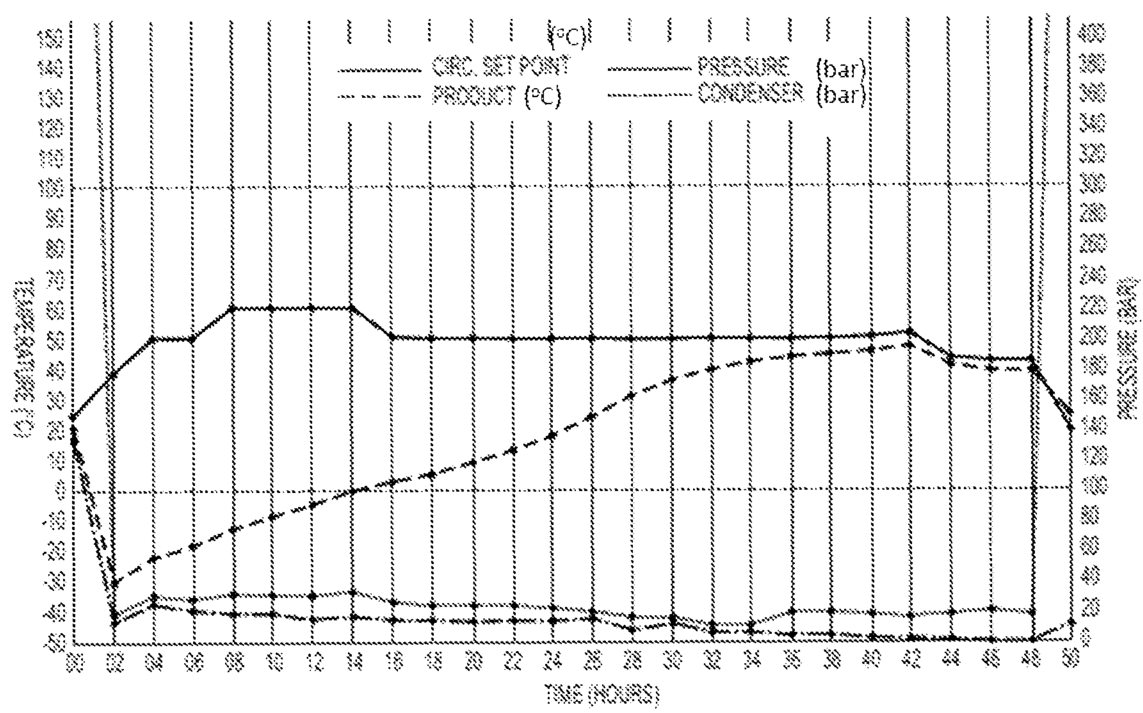
FIG. 1 depicts a graph showing a six-stage dryer profile of freeze drying the kiwifruit pulp according to the present invention.

Embodiments of the invention are discussed in detail below. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention. All references cited herein are incorporated by reference as if each had been individually incorporated.

In the description and examples that follow, all temperatures are set forth in uncorrected degrees Celsius. Pressures are presented alternatively in bar or Pascal (Pa), where 1 bar is equal to 100,000 Pa. Unless otherwise indicated, all parts and percentages are by weight. As used herein, the term "about" refers to plus or minus 10% of the indicated value. As used herein, the singular forms "a," "an," and "the" include plural referents unless the context clearly dictates otherwise. Water activity refers to the partial vapor pressure of something relative to the standard partial vapor pressure of water. Therefore, it is the relative humidity divided by 100. Water activity can be measured using a water activity meter, which detects the partial vapor pressure of the sample. As used herein, "substantially free" means that the component is present in amounts below what would generally be added to achieve the desired effect. For example, if a preservative is generally effective when present in an amount of 1% by weight, substantially free means the preservative is present in an amount less than about 1% by weight. In most cases, "substantially free" means that the ingredient is not added to achieve an effect. In most embodiments, "substantially free" means that the component is not intentionally added at all.

The present invention provides an all-natural dried *Actinidia deliciosa* powder from kiwifruit. The dried *Actinidia deliciosa* powder has a low moisture level and does not contain any additives or preservatives, but maintains a free-flowing character by using a blend of dried kiwifruit skin and dried kiwifruit pulp. Surprisingly and unexpectedly, the use of the dried kiwifruit skin in accordance with the present invention provides the final blended product with the needed flowability, while preventing the need of using any other excipients or anti-caking agents. The invention thus provides an all-natural supplement and powders that can be used to manufacture an all-natural supplement.

According to the present invention, the kiwifruit skin and the kiwifruit pulp are dried separately, for example by freeze drying. The nature of the skin fraction and in particular the water content varies due to residual flesh content. As such, it was found that simply using a fixed ratio of dried kiwifruit skin to dried kiwifruit pulp resulted in varying levels of actinidin enzyme activity in the final product. To achieve a consistent actinidin enzyme activity and low level of moisture in the final product, it was found to be beneficial to calculate the insoluble fiber in the dried kiwifruit skin and the dried kiwifruit pulp and combine the skin and pulp to achieve a desired content of insoluble fiber. A desired product with consistent actinidin enzyme activity and a low level of moisture can be achieved by blending dried kiwifruit skin with dried kiwifruit pulp to obtain a total insoluble fiber content of 10-20%, or most preferably 10-15% as measured using, for example, Megazyme method (AOAC 991.43). Specifically, the dried kiwifruit skin is added to the dried kiwifruit pulp in an amount to obtain an insoluble fiber content of 10-15% in the blend. The blend can be milled and formed into a tablet or filled into a capsule to provide a composition as a dietary or nutritional supplement.

The desired blend of the *Actinidia deliciosa* was best achieved by using a combination of radiant and conductive heating methods for the kiwifruit pulp and the kiwifruit skin, respectively. It was found that by separately preparing the dried components and storing at temperatures higher than room temperature before blending beneficially avoided the product from absorbing moisture. In addition, when the dried kiwifruit skin and the kiwifruit pulp are blended within 24 hours of their respective drying processes, the dried kiwifruit skin (dried at a higher temperature) provides a final drying atmosphere for the dried kiwifruit flesh and the blended product equilibrates to a desirable moisture level.

Drying Kiwifruit Pulp

The kiwifruit flesh or pulp contains actinidin enzyme, which is one of the beneficial components of the final product. The kiwifruit flesh can contain up to 30,000 units of actinidin enzyme activity. However, dried kiwifruit pulp is highly hydroscopic and without the use of excipients, the final product forms clumps and is difficult to work with during processing. In addition, actinidin enzyme activity is extremely sensitive to drying temperatures. Therefore, drying time and drying temperature must be balanced to achieve the desired actinidin enzyme in the dried product.

It was also found that different temperatures used during drying cycle for the pulp affect the actinidin enzyme activity in the final product. Specifically, the longer the kiwifruit pulp was held below 0° C. degrees during the drying process, the higher the actinidin enzyme activity. Holding the kiwifruit pulp below 0° C. during the drying process results in a product that is more free-flowing with a more homogenous blend. Moreover, more consistent actinidin activity is achieved.

In some embodiments of the present invention, the kiwifruit pulp is freeze dried using radiant heat in various stages. Each stage varies in temperature and time. Radiant heat drying provides a more uniform drying from top to bottom, and is less sensitive to uneven tray loading. Prior to freeze drying, the kiwifruit pulp is stored in cold storage below, for example from about −12° C. to about −20° C., or at about −16° C. The pulp is then processed at a temperature of <10° C. In embodiments, the kiwifruit pulp is passed through a mincer at less than −12° C., for example from about −12° C. to about −20° C. or at about −18° C. Mincing is conducted by crushing frozen blocks of kiwifruit pulp into a frozen ice slurry for loading on to the trays. In exemplary embodiments, the kiwifruit pulp is frozen at a temperature of less than about −25° C. before mincing. As will be appreciated by persons skilled in the art, batch size can vary depending on the size and type of equipment utilized. In some embodiments, the minced pulp is maintained at a temperature of less than about −30° C. for at least 4 hours before freeze drying the pulp. In other embodiments, the minced pulp is maintained at a temperature of less than about −30° C. for from about 10 to about 14 hours.

After mincing, the kiwifruit pulp is placed in plastic lined aluminum trays and transferred to a blast freezer and subject to blast freezing to a temperature of less than about −25° C., for example from about −25° C. to about −30° C. for at least 4 hours, at least 7 hours, or preferably, at least 10-14 hours. Then, the pulp is loaded to the freeze drier to begin the drying cycle.

FIG. 1 shows a dryer profile in accordance with an exemplary embodiment of the invention. The graph shows the temperature (° C.) and pressure vs. time of freeze drying the kiwifruit pulp. Drying of the kiwifruit pulp can be conducted in a number of stages under various drying temperature profiles. For example, the drying can range from four to eight stages, temperature for each stage can range from 30° C. to 50° C., the drying time for each stage can range from 30 minutes to 1800 minutes. Pressure also impacts the drying time and temperature of the drying process and can range from 60 Pa to 10 Pa. With the exemplary parameter and guidance described herein, persons skilled in the art may make some modifications to the detailed process and still obtain a satisfactorily dried kiwifruit pulp, for example a dried kiwifruit pulp with a moisture content of no more than 4% and a high actinidin enzyme activity, for example an actinidin enzyme activity of at least 100,000 AU/g. In this example, the drying is conducted in six stages. The first stage at 30° C. for 60 minutes; a second stage at 50° C. for 250 minutes; a third stage at 60° C. for 580 minutes; a fourth stage at 50° C. for 1320 minutes; a fifth stage at 40° C. for 640 minutes; and a sixth stage at 30° C. for 30 minutes. The pulp is freeze-dried under vacuum at a pressure between 45 Pa (0.00045 Bar) to 20 Pa (0.0002 Bar). The pulp is dried to a water activity of, for example, less than about 0.4, less than about 0.3, or less than about 0.2. The pulp is dried to a moisture content of less than about 5%, or less than about 4%.

It was found that by increasing the temperature to 60° C. at the third stage, the kiwifruit pulp was effectively dried at the end of the 50 hours drying cycle. The product was of low water activity (<0.2) and high enzyme activity over 180,000 AU/g. It is desirable that the product from the dryer have at least 150,000 AU/g enzymatic activities because this allows for loss during dilution or further processing. The final product can have actinidin enzyme activity of at least about 100,000 AU/g, preferably at least about 120,000 AU/g.

Using the present method, the batch size can be from 1,000 kg to 3,500 kg wet, yielding between about 180 kg to about 520 kg dry pulp. In embodiments, the batch size can be about 1,400 kg or about to 2,800 kg wet yielding about 225 kg or about 450 kg dry pulp, respectively.

Figure 2:
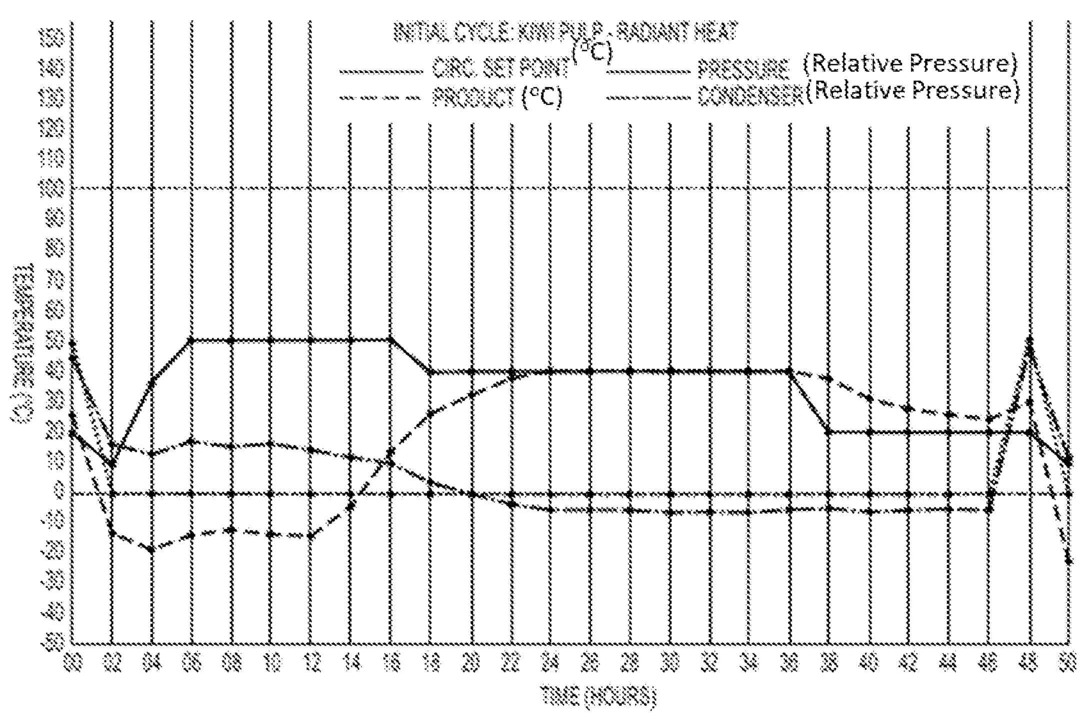
FIG. 2 depicts a graph showing a four-stage comparative dryer profile of freeze drying the kiwifruit pulp.

FIG. 2 shows the dryer profile of a four-stage comparative drying cycle. In comparison, when the kiwifruit pulp was dried using a four-stage drying profile at a maximum of 50° C., the product was not fully dried at the end of 50 hours.

After drying, the kiwifruit pulp is kept at room temperature in sealed bags and kept away from sunlight.

Drying Kiwifruit Skin

Due to its higher density, it was found particularly advantageous to dry the kiwifruit skin, for example by freeze drying, using conductive direct heat rather than radiant heat. Thus, in an embodiment of the present invention, the kiwifruit skin is freeze dried using conductive heat under various stages. Each stage varies in temperature and time. The drying temperature is selected such that the kiwifruit skin is not discolored and/or denaturation of any active enzyme is minimized. The kiwifruit skin contains varying amount of residual flesh. During drying of the kiwifruit skin, the actinidin enzyme activity in the skin may be reduced. While this loss of activity is preferably controlled, the actinidin enzyme activity in the kiwifruit skin, which is mostly due to the residual flesh, is less important because most of the actinidin enzyme activity in the final product is provided by the dried kiwifruit pulp.

Prior to freeze drying, the kiwifruit skin is stored at a temperature of less than about −12° C., for example, from about −20° C. to about −12° C. The skin is then processed at a temperature of <10° C. The kiwifruit skin is passed through a mincer to reduce the size of the skin. In exemplary embodiments, the dried skin is minced to a size of 16 mm before freeze drying. This process allows the skin to be efficiently blended with the dried kiwifruit pulp after drying. The kiwifruit skin is frozen at a temperature of less than about −25° C., for example from about −25° C. to about −30° C., for at least 4 hours, at least 7 hours, or preferably, at least 10-14 hours. The skin is then loaded to the freeze drier to begin the drying cycle.

Drying of the kiwifruit skin can be conducted in a number of stages under varies drying temperature profiles. For example, the drying can range from four to six stages, temperature for each stage can range from 30° C. to 90° C., and the drying time for each stage can range from 30 minutes to 1500 minutes. Pressure also impacts the drying time and temperature of the drying process and can range from 60 Pa to 10 Pa. With the exemplary parameters and guidance described herein, persons skilled in the art may make some modifications to the detailed process and still obtain a satisfactorily dried kiwifruit skin, for example a dried kiwifruit skin having a water activity of less than about 0.2 and a moisture content of less than about 1.5%. In an exemplary embodiment, the freeze-drying of the skin can include, a first stage at 10° C. for 180 minutes, a second stage at 70° C. for 1020 minutes, a third stage at 60° C. for 420 minutes, and a fourth stage at 50° C. for 90 minutes. The skin is freeze-dried under vacuum at a pressure less than 0.002 Bar. The temperature of any stage should not exceed 90° C. The skin is dried to a water activity of less than about 0.4, less than about 0.3, or preferably less than about 0.2. The skin is dried to a moisture content of less than about 3%, less than about 2%, or less than about 1.5%. In particular, the invention achieves a water activity for the dried kiwifruit skin less than about 0.2 and moisture level of 1%.

After drying, the product is kept at room temperature in sealed bags and kept away from sunlight.

It will be readily apparent to those skilled in the art that various changes and modifications may be made based on the teachings of the invention, and all such changes and modifications are considered to fall within the scope of the invention. Such changes and modifications may include the drying time, drying temperature, and pressure of the kiwifruit pulp and kiwifruit skin.

Blended Powdered Product

The blended powdered product is prepared by combining the dried kiwifruit pulp and dried kiwifruit skin obtained as above to obtain an insoluble fiber content of 10-20%, or preferably 10-15%. In an exemplary embodiment of the invention, the blended powder has an actinidin enzyme activity of from about 50,000 AU/g to about 200,000 AU/g, from about 50,000 AU/g to about 165,000 AU/g, or from about 100,000 AU/g to about 150,000 AU/g. In exemplary embodiments, the actinidin enzyme activity is at least about 50,000 AU/g, at least about 100,000 AU/g, at least about 120,000 AU/g, or at least about 150,000 AU/g. The powder according to exemplary embodiments of the invention has a moisture content of less than about 4%, less than about 3.0%, less than about 2.5%, or less than about 1.8%. For example, the powder according to exemplary embodiments of the invention can have a moisture content of from about 1.1% to about 4%, from about 1.5% to about 3.0%, or from about 1.8% to about 2.5%. The powder according to exemplary embodiments of the invention has a water activity of less than about 3.2, less than about 2.8, less than about 1.8, less than about 1.0, or less than about 0.2. The powder according to exemplary embodiments of the invention has a protein content of from about 2% to about 7.3%, from about 2.5% to about 6.8%, from about 3% to about 6%. The powder according to exemplary embodiments of the invention has a fat content of from about 0.1% to about 2%, from about 0.4% to about 1.7%, from about 0.5% to about 1.5%, or from about 0.7% to about 1.0%. The powder according to exemplary embodiments of the invention has an ash content (i.e., measured as the ash residue upon ignition) of from about 3.3% to about 5.4%, from about 3.7% to about 5.0%, or from about 3.9% to about 4.3%. The powder according to exemplary embodiments of the invention has a total carbohydrate content of from about 70% to about 98%, from about 75% to about 95%, or from about 80% to about 92%. The powder according to exemplary embodiments of the invention has a sugars content of from about 38% to about 70%, from about 42% to about 65%, or from about 45% to about 62%. In exemplary embodiments, the powder of the invention has a total dietary fiber content of from about 5% to about 25%, from about 8% to about 22%, or from about 10% to about 20%.

Kiwifruit are also known to contain relatively high amounts of serotonin. One study (Commisso, M. et al. *Int. J. Mol. Sci.* 20, 897 (2019), has found the serotonin content to be on the order of 0.55 mg/100 g of fresh kiwifruit. Utilizing the process of the present invention, losses in serotonin levels are minimized or avoided all together. For example, exemplary embodiments of the invention can provide serotonin in an amount of about 3.0 mg to about 5.0 mg/100 g dry weight (as combined dried pulp and skin). Based on an approximate yield of 15% on drying, this corresponds to about 0.45 mg to about 0.75 mg/100 g fresh kiwifruit. Some embodiments can have from about 3.4 mg to about 4.2 mg of serotonin/100 g dry weight. In some embodiments of the invention, the serotonin content of the dried kiwifruit pulp can be about 4.0 mg to about 5.0 mg/100 g, for example about 4.4 mg to about 4.5 mg/100 g. After blending, moisture absorption can happen quickly. Accordingly, after blending, the product is packaged in a clean and low humidity environment, placed in bags and heat sealed. The bagged product is kept at room temperature in sealed bags away from sunlight until further packaged or processed into a composition.

Table 1 below shows the exemplary properties of the dried pulp, dried skin, and blended powder according to embodiments of the present invention. The table also shows the content of the blended powder of the present invention.

TABLE 1

Exemplary Properties of the Dried Pulp, Dried Skin, and Blended Powder According to the invention

| | Pulp | Skin | Blended Powder |
|---|---|---|---|
| Moisture % | <4 | <1.5 | <4 |
| Water Activity | <0.2 | <0.2 | <0.2 |
| Protein % | 3-6 | 4-8 | 3-6 |
| Fat % | <1.5 | >1.5 | ≤1.5 |
| Ash % (residual upon ignition) | <10 | <5 | ≤5 |
| Total Carbohydrates % | >80 | <45 | ≥80 |
| Sugars % | 55-60 | 30-35 | ≥45 |
| Total Dietary Fiber % | 8-15 | 40-60 | ≥10 |
| Actinidin Enzyme AU/g | >150,000 | n/a | >100,000 |

As shown in Table 1, the *Actinidia deliciosa* powder of the invention has a moisture content in the range of 1.1% to 4%. The powder has a water activity in the range of less than about 0.32, for example about 0.2 or lower. The powder has a protein content in the range of about 3% and about 5.2%. The powder has a fat content in the range of about 0.1% to about 0.7%. The powder has a residual ash content on ignition in the range of 3.3% to 5.4%. The powder has a total carbohydrates content in the range of 80% to 92%. The powder has a sugars content in the range of 45% to 62%. The powder has a total dietary fiber content in the range of 10% to 20%. The powder has an actinidin enzyme activity greater than 50,000 AU/g, greater than 65,000 AU/g, and can be in the range of 100,000 AU/g to 150,000 AU/g.

Compositions

The blended powder of the invention can be used to manufacture a composition for use as a dietary supplement or nutritional supplement. The composition is prepared by, for example, forming the powder into a tablet or filling the powder into a capsule.

In exemplary embodiments, the composition is free of non-natural additives, anti-caking agents, or flow agents. In exemplary embodiments, the composition is substantially free of cellulose, silica, magnesium stearate, isomalt and other excipients. The actinidin enzyme activity in the composition is at least about 50,000 AU/g, at least about 100,000 AU/g, at least about 120,000 AU/g. The composition has a moisture content of less than about 4.0%, less than about 3.4%, less than about 2.7%, or less than about 1.8%. The composition has a water activity of less than about 3.2, less than about 2.4, less than about 1.8, less than about 1.3, or less than about 0.2. The composition has a protein content of about 3% to 6%. The composition has a fat content of from about 0.1% to about 1.5%, and can be less than about 0.4%, or less than about 1.0%. The composition has a residual ash content on ignition of less than about 6%, less than about 5.5%, and less than about 5%. The composition has a total carbohydrates content of at least about 40%, at least about 60%, or preferably at least about 70%. The composition has a sugars content of at least about 38%, preferably at least about 42%, preferably at least about 60.5%. Exemplary embodiments have a sugar content of about 45-65%. The composition has a total dietary fiber content of at least about 5%, preferably at least about 8%, or preferably at least about 10%. Exemplary embodiments have a fiber content of about 10-15%. The composition has an actinidin enzyme activity of at least about 50,000 AU/g, at least about 65,000 AU/g, at least about, 100,000 AU/g, or at least about 120,000 AU/g.

EXAMPLES

The following examples are given to illustrate various embodiments which have been made or may be made in accordance with the present invention. These examples are given by way of examples only, and it is to be understood that the following examples are not comprehensive or exhaustive of the many possible embodiments of the present invention.

Example 1—Method of Preparation

In a generalized method, the following steps are used to prepare a product according to the invention:

1) Separated Kiwifruit (*Actinidia deliciosa*) flesh and skins are sourced from a primary processor. The kiwifruit flesh (pulp) and skin are transported under refrigeration and stored frozen at a temperature of below −12° C.
2) Decartoned—removing the flesh and skin from packaging in processing rooms at a temperature of below 10° C.
3) Minced—the flesh is passed through a mincer at a temperature of −12° C. and the skin is passed through a mincer. Both the flesh and the skin are reduced in size during the mincing process. The flesh is then placed into a blast freezer at a temperature of −25° C.
4) Loaded onto trays—the flesh and the skin are loaded separately onto trays.
5) Frozen down—the flesh is dried using radiant heat and the skin is dried using conductive heat.
6) Dried until ≤4% moisture remains
7) Blend to correct flesh/skin ratio—the dried flesh and the dried skin are blended together to achieve an insoluble fiber content of between 10-15%.
8) Milled into a fine powder of required mesh size
9) Packed into foil laminate bags in lined cardboard cartons.
10) Samples are taken for microbial and chemical testing Example 2—Measurement of Actinidin Activity Actinidin activity is measured using the following method, which describes the procedure for estimating the amount of actinidin activity in freeze dried kiwifruit using the artificial colorimetric substrate $N_{\alpha}$-Z-L-lysine 4-nitrophenyl ester (z-Lis-pNP).

A. Materials

1. Phosphate buffer:

50 mM phosphate pH 6.0

Solution A: 2.17 g of $Na_2HPO_4 \cdot 2H_2O$ in 250 mL deionised, distilled water Solution B: 7.80 g of $NaH_2PO_4 \cdot 2H_2O$ in 1000 mL deionised distilled water Add solution A to solution B until the pH is 6.0.

2. EDTA Stock 50 mM:

Ethylenediaminetetraacetic acid: Formula weight 292.24 g/mol.

Weigh approximately 20 mg of EDTA into a 1.5-2 mL vial. Divide the weight in mg by 14.654 to determine the correct amount of water to add in mL to obtain a 50 mM solution. The stock can be kept frozen to be used as required.

3. DTT Stock 500 mM (prepare fresh daily):

Dithiothreitol: Formula weight 154.25 g/mol

Weigh 15 to 30 mg DTT into a 1-2 mL vial. Divide the weight in mg by 77.13 to determine the correct amount of water to add in mL to obtain a 500 mM solution.

4. Substrate Stock:

N-a-CBZ-lys-p-nitrophenol (Z-Lys-OpNP HCl) CAS No. 2179-15-9

Sigma Aldrich 96895. Formula weight 437.87 g/mol 4 mM z-Lys-pNP solution: Dissolve 43.7 mg in 25 mL of milliQ water. Freeze in 1 mL aliquots. Upon thawing a brief sonication is useful to disperse any undissolved precipitate. Keep thawed solution on ice and use within 120 minutes. Do not refreeze after thawing.

B. Sample Preparation:

Accurately weigh approximately 0.5 g kiwifruit powder and add 9 mL phosphate buffer (50 mM pH 6.0); thoroughly mix and adjust volume to 10 mL. Centrifuge at 4000 rcf for 10 min. Dilute the supernatant 2-fold by adding 200 μL supernatant to 160 μL phosphate buffer, 20 μL EDTA stock and 20 μL DTT Stock.

A blank sample containing: 360 μL phosphate buffer, 20 μL EDTA stock and 20 μL DTT Stock is required.

C. Assay:

Spectrophotometer temperature set to 25° C.

900 μL Phosphate buffer (50 mM pH6.0)

+50 μL Sample (DTT and EDTA affect the rate of Z-Lys-pNP degradation so it is important to have the correct amount of each in a blank sample)

+50 μL Z-Lys-pNP (reaction concentration 200 μM)

Continuously read the absorbance at 348 nm for 90 seconds. Record the rate of change in absorbance during the near linear region, typically between 12 and 30 seconds.

Assay each sample in triplicate.

D. Activity Calculations:

1)

$$\text{Activity} = \frac{\text{sample rate} - \text{blank rate}}{\Delta\varepsilon} = M \cdot \text{min}^{-1}$$
$$\text{where } \Delta\varepsilon = 5400$$

2) $M \cdot min^{-1} \times 0.001$ L=$mol \cdot min^{-1}$ where 0.001 is the assay volume 3) $mol \cdot min^{-1} \times 10^6 = \mu mol \cdot min^{-1}$

4)

$$\frac{\mu\text{mol min}^{-1}}{\left(\frac{\text{sample } c.a.\ 0.2 \text{ g}}{10 \text{ mL}} \times \frac{0.05 \text{ mL}}{\text{dilution } i.e.\ 2}\right)} = \mu\text{mol} \cdot \text{min}^{-1} \cdot \text{g}^{-1}$$

Note that this calculation is for an assay carried out in a 1 cm path length cuvette.

Example 3—Measurement of Insoluble Fiber

The insoluble fiber content was tested using known Megazyme method, including AOAC991.43.

Example 4—Characteristics of Powder

An *Actinidia deliciosa* powder produced in accordance with the present invention was prepared as a fine, naturally free-flowing green to brown powder, containing no artificial additives, anti-caking or flow agents. The end product has the analysis as shown in Table 2.

TABLE 2

Analysis of Powder

| Proximate Analysis | Analysis | Test Method |
|---|---|---|
| Moisture % | <4 | AOAC 950.46 OMA |
| Fat % | ≤1.5 | AOAC 18$^{th}$ edition 960.39 |
| Protein % | 3-6 | AOAC 18$^{th}$ edition 981.10 |
| Ash (Residue on Ignition) % | ≤5 | AOA3C 18$^{th}$ edition 938.08 |

TABLE 2-continued

| Analysis of Powder | | |
|---|---|---|
| Proximate Analysis | Analysis | Test Method |
| Total Carbohydrate (by calculation) % | ≥60 | By calculation |
| Sugars % | 45-65 | Phenol Sulphuric |
| Total Dietary Fiber % | 10-15 | Megazyme, AOAC 18$^{th}$ Edition 991.43 |
| Actinidin Enzyme AU/g | >20,000 | z-Lys-pNP substrate |
| Heavy Metal Analysis | | |
| Lead ppm | <1 | ICP-MS |
| Cadmium ppm | <1 | ICP-MS |
| Mercury ppm | <0.1 | ICP-MS |
| Microbiological Analysis | | |
| Total Aerobic Count (TAC)(48 hrs@35° C. cfu/g) | <50,000 | APHA 4$^{th}$ Ed. 2001, Ch. 7 |
| *Escherichia coli* (mpn/g) | <10 | APHA 4$^{th}$ Ed. 2001, Ch. 8 |
| *Salmonella* (per 25 g) | Absent | ISO 6579 |
| Yeasts and Moulds (mpn/g) | <1000 | APHA 4$^{th}$ Ed. 2001, Ch. 10.5 |

Example 5—Comparative Example

Table 3 compares properties of a Comparative Example A with Inventive Examples 1 and 2. Comparative Example A was prepared from kiwifruit flesh only, which was dried using conductive heat on a 36-48 hour cycle. Moisture content was <5% and water activity was 0.3. Inventive Example 1 was prepared according to the invention using five drying stages as follows:

Stage 1: 30° C. for 55 minutes;
Stage 2: 40° C. for 80 minutes;
Stage 3: 50° C. for 2260 minutes;
Stage 4: 40° C. for 455 minutes; and
Stage 5: 30° C. for 30 minutes.

Inventive Example 2 was prepared using six drying stages as follows:

Stage 1: 30° C. for 60 minutes;
Stage 2: 50° C. for 250 minutes;
Stage 3: 60° C. for 580 minutes;
Stage 4: 50° C. for 1320 minutes;
Stage 5: 40° C. for 640 minutes; and
Stage 6: 30° C. for 30 minutes.

TABLE 3

Comparison of Invention to Dried Kiwifruit Pulp

| | Comparative Example A | Inventive Example 1 | Inventive Example 2 |
|---|---|---|---|
| Moisture % | 4.5 | 2.4 | 1.8 |
| Water Activity | 0.3 | 0.2 | 0.2 |
| Protein % | — | 4.4 | 4.9 |
| Fat % | — | 0.4 | 0.43 |
| Ash % | — | 3.8 | 4.1 |
| Total Carbohydrates % | — | — | — |
| Sugars % | — | 56.4 | 60.5 |
| Total Dietary Fiber % | 15 | 15.3 | 14.6 |
| Actinidin Enzyme AU/g | 67,700 | 127,400 | 155,500 |

As shown in Table 3, Comparative Example A had a moisture content of <5% and a water activity of 0.3. Inventive Example 1 has an actinidin enzyme activity of 127,400 AU/g, which almost double the enzyme activity of Comparative Example A, and a moisture level of 2.4%, which is significantly lower than the moisture level of Comparative Example A. Inventive Example 2 has an even lower the moisture level of 1.8% and a further increased actinidin enzyme activity of 155,500 AU/g.

Example 6—Serotonin Content

The serotonin content of kiwifruit pulp and the final kiwifruit product of the present invention was measured and the results shown in Table 4 below.

TABLE 4

Serotonin Content of Dried Kiwifruit Powder and Pulp

| Sample Description | Serotonin Content mg/100 g DW) | ±SEM |
|---|---|---|
| Actiphen Freeze dried kiwifruit powder (Sample 1) | 3.42 | 0.05 |
| Actiphen Freeze dried kiwifruit powder (Sample 2) | 4.17 | 0.19 |
| Actiphen Freeze dried green kiwifruit puree-no skin | 4.45 | 0.20 |

DW = Dry weight
SEM = Standard error of the mean

The Limit of detection (LOD) at 5× signal/noise was 0.11

Example 7—Clinical Study

Purpose of Study

This study was designed to assess the effectiveness of Inventive Composition on gastrointestinal tract (GIT) function, including bowel frequency, bloating, flatulence and abnormal pain.

Product

The composition prepared according to the invention was provided in vegetarian microcrystalline hard shell 2-piece capsules, filled at a GMP compliant manufacturing facility. The product included two active treatment arms; Arm A utilized the composition in a 1000 mg dose which included 6×167 mg of the composition plus 533 mg maltodextrin (total capsule fill weight 700 mg), and Arm B utilized a 3000 mg dose which included 6×500 mg of the composition+200 mg maltodextrin (total capsule fill weight 700 mg). The placebo contained 6×700 mg maltodextrin (total capsule fill weight 700 mg) and was housed in a capsule identical in appearance to the test product. The daily dose for all treatment arms was 6 capsules taken orally at breakfast time with food and 250 ml of water for a period of 6 weeks.

This trial was conducted in compliance with the current International Conference on Harmonization (ICH), Guideline for Good Clinical Practice (GCP), the Therapeutic Goods Administration (TGA), Notice for Guidance on Good Clinical Practice and ethical guidelines outlined in Additional Ethical Considerations. It was approved by Bellberry Limited Human Research and Ethics committee (approval number 201712968) and registered on the Australia New Zealand Clinical Trials Registry ACTRN12618000875202.

Methods

Participants

Data are reported for 24 completed participants, healthy males and females aged over 18 years were recruited from Brisbane, Australia and surrounding areas.

Following preliminary screening via telephone, eligible potential participants attended the clinic for an information session and provided consent for inclusion into the trial. Enrollment in the trial to receive product occurred only after all inclusion criteria were met. Male and female participants were included if they were over 18 years of age, had normal dietary habits, agreed not to change their diet and exercise regime, agreed not to use other dietary supplements targeted to gut health, able to provide informed consent and experienced three or more of the following symptoms for at least 3 days in the 3 months before enrolment into the study: bloating, flatulence, diarrhea, constipation, reflux, heart burn, and abdominal pain/discomfort. Participants were excluded if they had significant medical conditions, had a history of inflammatory bowel disease or gastrointestinal tract surgery, pregnant or lactating women, smoked, consumed more than 2 standard alcoholic drinks daily, allergic to kiwi fruit, had a history of infection, worked nightshifts, or suffered acute or chronic inflammation.

Eligible participants provided consent and undertook a health assessment which included lifestyle, blood pressure, heart rate, current medications, medical history, body composition, dietary intake, GIT function (questionnaire), quality of life (fatigue). Participants further undertook a macular pigment optical density (MPOD) test, and blood collection, which will be analysed for lutein, serotonin and zonulin concentration.

Participants were asked to take the allocated product according to the prescribed dose and attended the study site at weeks 3 and 6 for further body composition assessment, and questionnaires. Between visits, participants recorded the number of daily bowel movements in a stool frequency diary. During the final appointment at week 6, assessment identical to baseline was conducted.

Outcome Measures

The primary outcome measure of this study was change in GIT function with stool frequency as the primary focus. Secondary outcome measures included change in GIT function (The Patient Assessment of Constipation Quality of Life Questionnaire, Gastrointestinal Symptom Rating Scale, IBS Symptom Scoring System, Bristol Stool Chart), change in GIT permeability (plasma zonulin), change in quality of life and fatigue (SF36 questionnaire), change in plasma lutein, change in MPOD score (MPS II Macular Pigment Screener), change in sleep quality (Pittsburgh Sleep Quality Assessment), and adverse reactions and gastrointestinal tolerance (GIT Tolerance questionnaire).

Preliminary Results

Data presented herein is a snapshot of initial results for the purposes of assessment. The data analyzed is for two treatment groups only, Placebo (n=13) and (n=11) the higher dose of 3000 mg of the composition per day at baseline and final appointments only. Blood analysis has not yet been undertaken.

TABLE 5

Demographic Data

| | Baseline | | Week 6 | |
|---|---|---|---|---|
| | Invention | Placebo | Invention | Placebo |
| Age | 44.2 ± 14.8 | 45.2 ± 14.9 | NA | NA |
| Waist circumference (cm) | 87.0 ± 14.8 | 87.3 ± 10.3 | 88.9 ± 14.7 | 85.5 ± 10.5 |
| Hip circumference (cm) | 104.1 ± 10.4 | 103.6 ± 7.7 | 103.5 ± 10.1 | 103.4 ± 8.9 |
| Waist to hip ratio | 0.83 ± 0.06 | 0.84 ± 0.06 | 0.85 ± 0.07 | 0.82 ± 0.05 |
| Systolic blood pressure | 120.3 ± 14.4 | 121.9 ± 16.5 | 122.2 ± 11.9 | 115.0 ± 14.4 |
| Diastolic blood pressure | 78.2 ± 7.9 | 74.4 ± 12.2 | 81.0 ± 7.7 | 75.2 ± 9.7 |
| Heart rate (bpm) | 68.8 ± 6.7 | 62.0 ± 8.5 | 69.1 ± 5.8 | 64.7 ± 9.6 |
| Height (cm) | 167.7 ± 4.8 | 168.7 ± 13.5 | 169.1 ± 5.7 | 168.5 ± 13.2 |
| Weight (kg) | 70.2 ± 14.2 | 72.4 ± 16.2 | 73.1 ± 14.4 | 72.4 ± 16.5 |
| Body mass index (m/kg$^2$) | 24.9 ± 4.8 | 25.2 ± 3.2 | 25.5 ± 4.7 | 25.3 ± 3.5 |

TABLE 6

Stool Consistency and Frequency

| | Baseline | | Week 6 | |
|---|---|---|---|---|
| | Inventio | Placebo | Inventio | Placebo |
| Stool number per week | 11.3 ± 5.8 | 10.3 ± 5.3 | 11.3 ± 4.7 | 10.8 ± 5.3 |
| Stool consistency (Bristol stool chart) | 3.8 ± 1.7 | 3.2 ± 1.5 | 4.0 ± 1.5 | 3.4 ± 1.3 |

TABLE 7

Gastrointestinal Symptom Rating Scale (GSRS) and Irritable Bowel Symptom Severity (IBSS) Score

| | Baseline | | Week 6 | |
|---|---|---|---|---|
| | Invention | Placebo | Invention | Placebo |
| GSRS | 8.3 ± 2.3 | 8.3 ± 2.4 | 5.7 ± 2.3* | 6.9 ± 4.2 |
| IBSSS | 21.3 ± 6.8 | 16.3 ± 3.8 | 10.7 ± 6.7* | 13.8 ± 9.0 |

*denotes a difference from baseline ($p < 0.05$)

Figure 3:
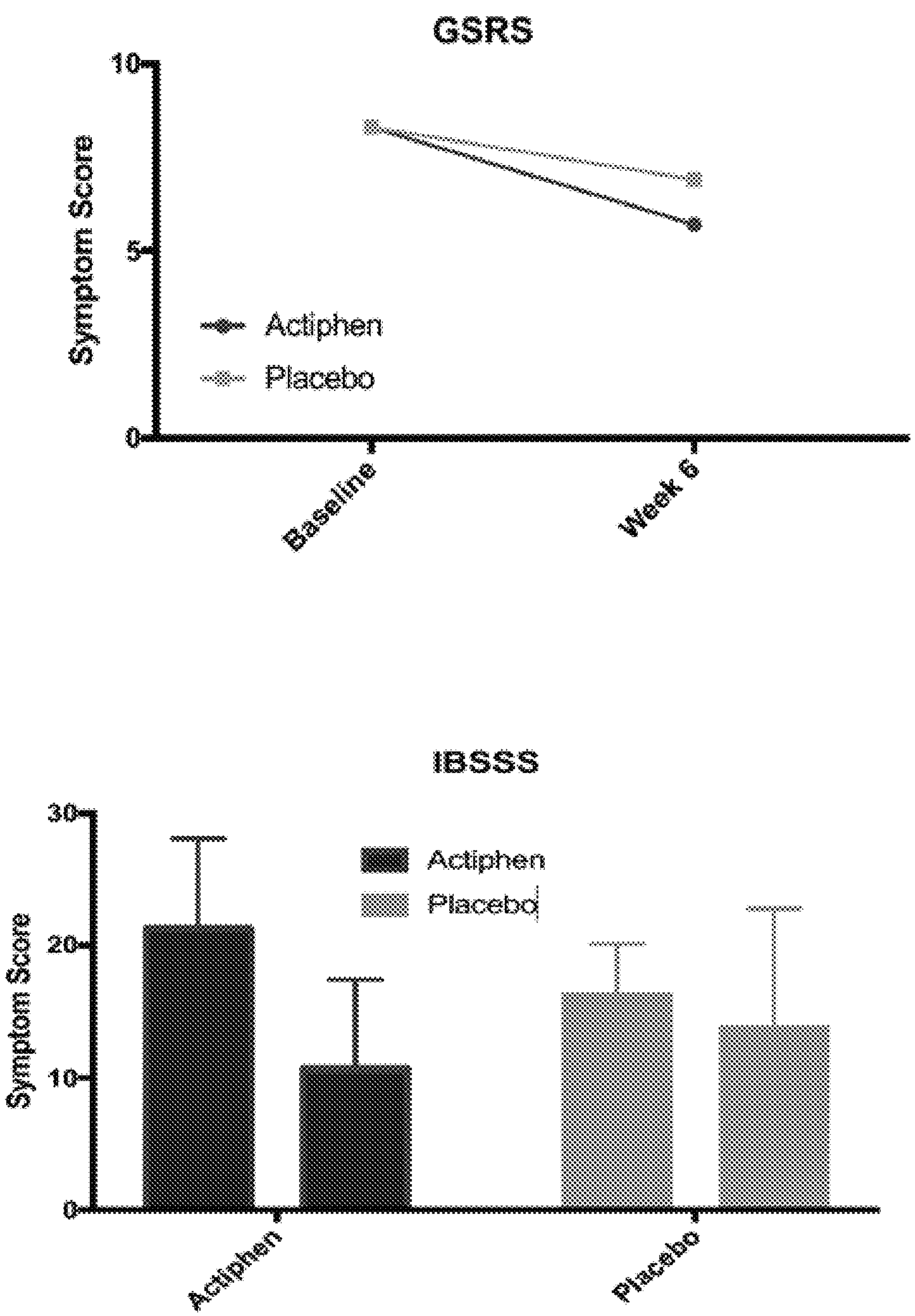
FIG. 3 graphically illustrates the Gastrointestinal Symptom Rating Scale (GSRS) and Irritable Bowel Symptom Severity (IBSS) Scores from a clinical trial using an embodiment of the invention.

FIG. 3 graphically illustrates the GSRS and IBSSS Symptom Scores

TABLE 8

| Macula pigment optical density testing | | | | | | |
|---|---|---|---|---|---|---|
| | Baseline | | Week 6 | | Δ | |
| | Invention | Placebo | Invention | Placebo | Invention | Placebo |
| MPOD left eye | 0.49 ± 0.23 | 0.39 ± 0.18# | 0.41 ± 0.17 | 0.47 ± 0.15 | −0.08 ± 0.11* | 0.07 ± 0.14 |
| MPOD right eye | 0.49 ± 0.13 | 0.38 ± 0.20 | 0.49 ± 0.17 | 0.45 ± 0.16 | 0.01 ± 0.09 | 0.07 ± 0.15 |

indicates a significant difference between groups at baseline ($p < 0.05$),
*indicates a significant difference in change between groups ($p < 0.05$)

Discussion

There were no differences in any demographic data from baseline to week 6. The number of stools per week and consistency of stools did not change from baseline to week 6 in either group, however, this is difficult to analyse on a group basis. Individual results varied with some participants improving both consistency and frequency.

Compositions according to the invention significantly improved responses to the gastrointestinal symptom rating scale and the irritable bowel syndrome severity score. The inventive composition was also associated with a ~50% reduction in IBSSS total. IBSSS rates symptoms such as abdominal pain, abdominal distension, satisfaction with bowel movements, and how bowel habits interfere with everyday life. Further analysis of the individual questions in the IBSSS and GSRS will be undertaken to ascertain the individual changes in specific symptoms.

There was a slight difference in MPOD score in the left eye at baseline between groups. This is most likely due to low participant numbers. There was a difference in the change score from baseline to week 6 between groups, however, this is most likely regression to the mean. A larger sample size will most likely reduce the variation in these results.

CONCLUSION

These initial results indicate that compositions according to the invention (3000 mg/day) significantly reduced the severity of Gastrointestinal and IBS symptoms as compared to placebo and improved quality of life.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

REFERENCES

1. Han K S. et al (2011) Green kiwifruit modulates the colonic microbiota in growing pigs. Letters in applied Microbiology 52, 379-385
2. Vesterlund S. et al (2012) Water activity in dry foods containing live probiotic bacteria should be carefully considered: A case study with *Lactobacillus rhamnosus* GG in Flexseed. International Journal of Food Microbiology 157, 319-321.
3. Neha A. et al (2012) Probiotic: as effective treatment of diseases. International Research Journal of Pharmacy 3 (1) 96-101.
4. Schroder R. et al (2001) Purification and characterization of a galactoglucomanna from kiwifruit (*Actinidia deliciosa*). Carbohydrate Research 331, 291-306.
5. Cal-Vidal J. et al (1985) Processing conditions affecting the hygroscopic behavior of freeze-dried passion fruit juice. Journal of Food Science 50, 1238-1241.

What is claimed is:

1. A method for producing stable and bioavailable *Actinidia deliciosa* powder from kiwifruit, comprising the steps of:

a) forming a minced kiwifruit pulp by mincing the kiwifruit pulp at a temperature of less than −18° C.;

b) freeze-drying the minced kiwifruit pulp by i) a freezing step comprising blast freezing the minced kiwifruit pulp to a temperature of less than −30° C. in a period of less than 3 hours; and ii) a drying step comprising drying the minced kiwifruit pulp to form dried pulp in a first stage at 30° C. for 60 minutes, a second stage at 50° C. for 250 minutes, a third stage at 60° C. for 580 minutes, a fourth stage at 50° C. for 1320 minutes, a fifth stage at 40° C. for 640 minutes, and a sixth stage at 30° C. for 30 minutes; or a first stage at 30° C. for 55 minutes, a second stage at 40° C. for 80 minutes, a third stage at 50° C. for 2260 minutes, a fourth stage at 40° C. for 455 minutes, and a fifth stage at 30° C. for 30 minutes;

wherein the dried pulp has an enzyme activity of at least 150,000 AU/g;

c) separately freeze-drying kiwifruit skin to form a dried skin that has a water activity of less than 0.2 or a moisture level of less than 1%;

d) measuring insoluble fiber content of the dried pulp and the dried skin; and e) forming a blend by blending the dried skin and dried pulp by adding the dried skin to the dried pulp in an amount to obtain an insoluble fiber content of 10-15% in the blend.

2. The method of claim 1, wherein the drying step of the freeze-drying the minced kiwifruit pulp uses radiant heat.

3. The method of claim 2, wherein the drying step of the freeze-drying the minced kiwifruit pulp comprises the steps of:

the first stage at 30° C. for 60 minutes,
the second stage at 50° C. for 250 minutes,
the third stage at 60° C. for 580 minutes,
the fourth stage at 50° C. for 1320 minutes,
the fifth stage at 40° C. for 640 minutes, and
the sixth stage at 30° C. for 30 minutes.

4. The method of claim 1, wherein the drying step of the freeze-drying the minced kiwifruit pulp is under vacuum at a pressure between 45 Pa (0.00045 Bar) to 20 Pa (0.0002 Bar).

5. The method of claim 1, wherein the dried pulp has a water activity of less than about 0.3 or a moisture level of less than 2.5%.

6. The method of claim 1, further comprising maintaining the minced kiwifruit pulp at a temperature of less than about −30° C. for at least 4 hours before the freeze-drying the minced kiwifruit pulp step.

7. The method of claim 6, wherein the minced kiwifruit pulp is maintained at a temperature of less than −30° C. for from about 10 hours to 14 hours before the freeze-drying the minced kiwifruit pulp step.

8. The method of claim 1, wherein the freeze-drying kiwifruit skin step comprises a drying step that uses conductive heat.

9. The method of claim 8, wherein the freeze-drying kiwifruit skin step comprises a drying step that comprises:

a first stage at 10° C. for 180 minutes;

a second stage at 70° C. for 1020 minutes;

a third stage at 60° C. for 420 minutes; and a fourth stage at 50° C. for 90 minutes.

10. The method of claim 9, wherein the freeze-drying kiwifruit skin step comprises a drying step under vacuum at a pressure less than 0.002 Bar.

11. The method of claim 2, wherein the drying step of the freeze-drying the minced kiwifruit pulp comprises:

the first stage at 30° C. for 60 minutes, the second stage at 50° C. for 250 minutes, the third stage at 60° C. for 580 minutes, the fourth stage at 50° C. for 1320 minutes, the fifth stage at 40° C. for 640 minutes, and the sixth stage at 30° C. for 30 minutes.

* * * * *